United States Patent [19]

Chandler et al.

[11] Patent Number: 4,769,216

[45] Date of Patent: Sep. 6, 1988

[54] DEVICE FOR DETECTING ANTIGENS AND ANTIBODIES

[75] Inventors: Howard M. Chandler, Kangaroo Ground; Kevin Healey, Niddrie; John G. R. Hurrell, Strathmore, all of Australia

[73] Assignee: Commonwealth Serum Laboratories Commission, Victoria, Australia

[21] Appl. No.: 836,779

[22] Filed: Mar. 6, 1986

Related U.S. Application Data

[62] Division of Ser. No. 413,364, filed as PCT AU81/00191 on Dec. 22, 1981, Published as WO82/02211 on Jul. 8, 1982, Pat. No. 4,590,157.

[30] Foreign Application Priority Data

Dec. 22, 1980 [AU] Australia .............. PE7043

[51] Int. Cl.$^4$ ............ C12Q 1/58; G01N 31/22
[52] U.S. Cl. ..................... 422/58; 422/61; 422/100; 435/12; 435/810; 436/808
[58] Field of Search ........ 422/57, 58, 59, 61, 422/69, 71, 100; 435/810, 7, 12; 436/807, 808, 809, 810

[56] References Cited

U.S. PATENT DOCUMENTS

| 3,036,894 | 5/1962 | Forestiere | 422/61 |
| 3,802,843 | 4/1974 | Kim | 422/71 |
| 3,865,552 | 2/1975 | Marston | 436/810 |
| 4,058,370 | 11/1977 | Suovaniemi | 422/100 |
| 4,087,248 | 5/1978 | Miles | 436/808 |
| 4,138,474 | 2/1979 | Updike | 436/810 |
| 4,272,478 | 6/1981 | Vihko | 422/57 |

Primary Examiner—Barry S. Richman
Assistant Examiner—Jill Johnston
Attorney, Agent, or Firm—Sughrue, Mion, Zinn, Macpeak & Seas

[57] ABSTRACT

A device for use in detecting or determining the presence of antigenic or haptenic substances or antibodies in a sample comprises a plurality of tubular or capillary elements (1, 2, 3, 4, 5, 6), each having antibodies or antigenic or haptenic substances attached to an internal surface thereof, and means (11) for causing fluids to pass simultaneously or sequentially through the plurality of capillary elements. A method and test kit for detecting and determining the presence of antigenic or haptenic substances or antibodies in a sample by the enzyme-linked immunosorbent assay technique is characterized by use of urease as the enzyme in an antibody-enzyme or antigen-enzyme conjugate, with urea being used as the enzyme substrate and the presence of ammonia being detected or determined using di-bromo-o-cresolsulfonphthalein.

8 Claims, 2 Drawing Sheets

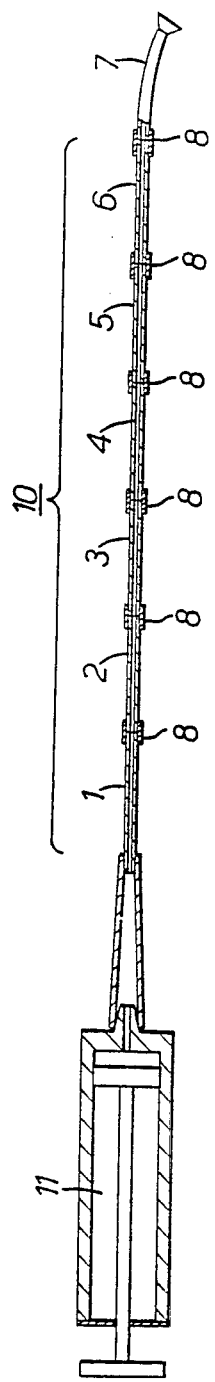
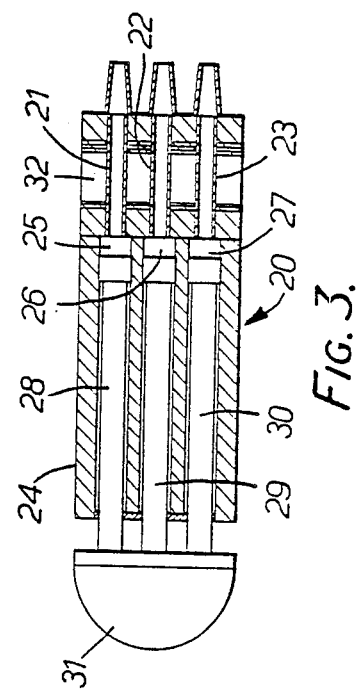

DEVICE FOR DETECTING ANTIGENS AND ANTIBODIES

This is a division of application Ser. No. 413,364 filed as PCT AU 81/00191 on Dec. 22, 1981, published as WO 82/0221 on Jul. 8, 1982 now U.S. Pat. No. 4,590,157.

This invention relates to improvements in methods, test kits and apparatus for performing enzyme-linked immunosorbent assays for the detection and quantitative determination of antigens and antibodies. In particular, the present invention relates to improvements in methods, test kits and apparatus which enable such assays to be performed by following a simple procedure which does not require the use of elaborate laboratory equipment or trained laboratory personnel, and hence may be performed under relatively adverse conditions, for example in the field.

In prior Australian Patent Specification No. 68117/81, there are described improved methods and apparatus for the performance of enzyme-linked immunosorbent assays (ELISA), which are particularly described with reference to their use in the detection of anti-tetanus antibodies in sheep and the detection and identification of snake venoms as examples of such assays.

The prior specification describes apparatus for detecting or determining the presence of antigenic or haptenic substances or antibodies in a sample which comprises a plurality of containers, one of said containers being provided with a cap which has antibodies or antigenic or haptenic substances attached to an internal surface thereof, said cap being adapted to be transferred from one to another of said containers so the internal surface thereof is brought into contact with solutions contained in said plurality of containers in a predetermined sequence. In one embodiment the "internal surface" of the cap includes those surfaces of the cap themselves which, when the cap is applied to a container, are exposed to the contents of the container, as well as the surfaces of projecting portions provided on the cap to extend within the body of the container when the cap is applied thereto, and surfaces which are physically attached to or retained within a cap which are themselves exposed to the contents of the container when the cap is applied thereto. In an alternative embodiment, the "internal surface" of the cap to which the antibodies or antigenic or haptenic substances are attached comprises the internal surface of a tube attached to the cap, for example the tube portion of a "dropper-type" cap having a rubber teat or the like to enable the fluid to be drawn up into the tube and expelled therefrom.

One of the main limitations of the apparatus disclosed in the prior specification lies in the fact that only a single antibody or antigenic or haptenic substance can be attached to the internal surface of the cap or of the tube attached to the cap. This is a relatively serious limitation when the apparatus is to be used in a screening-type test. For example, in the detection and identification of snake venoms in Australia, it is usually necessary to be able to detect at least two and in most cases five primary snake venoms to enable selection of the appropriate antivenom. This means that when using the apparatus disclosed in the prior specification, at least two and often five separate tests must be carried out in order to identify the unknown venom in the clinical sample, together with control tests where appropriate. The necessity to carry out a number of separate tests is, of course, particularly disadvantageous from the point of view of carrying out the necessary tests in the field, and it is an object of the present invention to provide a further improvement in this apparatus whereby the requirement for performing a plurality of separate tests may be avoided.

According to a first aspect of the present invention there is provided a device for use in detecting or determining the presence of antigenic or haptenic substances or antibodies in a sample, which device comprises a plurality of tubular or capillary elements, each of said capillary elements having antibodies or antigenic or haptenic substances attached to an internal surface thereof, and means for causing fluids to pass simultaneously or sequentially through said plurality of capillary elements.

In use of the device of this aspect of the invention, fluids including unknown samples and test reagents may be drawn in to the device and hence into contact with the internal surface of each of the capillary elements, and subsequently expelled therefrom. By way of example, such means may comprise a rubber teat or a syringe device.

The device of the present invention is particularly intended for use with test apparatus of the type generally disclosed in the prior Australian Specifications referred to above. Thus, the device of the present invention may be provided in combination with a plurality of containers whereby an assay may be performed by bringing the internal surfaces of the capillary elements of the device into contact with solutions contained in said plurality of containers in a predetermined sequence. Alternatively, the various test solutions and reagents may be provided in the wells of a reagent tray.

In general, the capillary elements comprising the device of the present invention may be made of any suitable material such as glass, polyvinyl chloride, polystyrene or other suitable plastics materials, however it is important that the elements be transparent so that reactions taking place within each element may be observed externally. The antibodies or antigenic or haptenic substances may be attached to the internal surface of the capillary elements by known techniques, for example, in the case of glass capillary elements, by adsorption or covalent bonding, and in the case of elements of plastics materials, by adsorption or covalent bonding. By way of example, the capillary elements may be 1.5 cm to 2.0 cm in length, and have an internal diameter of about 1 mm, and an external diameter of about 2 mm. Such elements have a capacity of around 5-20 $\mu l$.

In one embodiment of the device of this invention, the plurality of capillary elements are connected in series by tubular connecting elements. In this embodiment, fluids such as unknown samples and test reagents are drawn into and expelled from the elements in sequence. The tubular connecting elements inter-connecting the individual tubular elements may be of any suitable material, and by way of example, silicone rubber and polyvinyl chloride have been found to be suitable materials.

It will be appreciated that in general terms, the use of a device of the present invention enables a single sample to be "screened" against a number of known antibodies or antigenic or haptenic substances in a single test sequence. In such a "screening" assay, each capillary element will be provided with a different known antibody or antigenic or haptenic substance, and a "positive control" capillary element may also be included in the device. In order to test the unknown sample against each of the antibodies or antigenic or haptenic substances attached to the internal surfaces of the capillary elements, it is only necessary to perform a single test sequence by drawing the various test fluids in sequence into the device of the present invention so that each fluid passes into all the capillary elements before it is expelled from the device. One particular example of the use of the device of the present invention in this manner in the performance of an ELISA assay for the detection of snake venoms will be described in detail hereinafter.

Alternatively, the device of this invention may be used in a semi-quantitative type of "screening" test in which a single unknown sample is tested alongside one or more known positive controls against a single antibody or antigenic or haptenic substance in a single test sequence. The known positive control or controls may have known levels of the material which is to be detected in the sample, and once again the single test sequence is performed by drawing the various test fluids in sequence into the device and hence into the capillary elements before being expelled therefrom. The use of this device in this manner in the performance of digoxin and tetanus screening tests is described below as further examples of the use of this device.

In another aspect, the present invention relates to an improved method of detecting or determining the presence of antibodies or of antigenic or haptenic substances in a sample. Prior Australian Specification No. 68117/81 discloses tests for the detection or determination of the presence of antibodies or antigenic or haptenic substances by an improved enzyme-linked immunosorbent assay procedure in which the enzyme urease is used in the antibody-enzyme conjugate, with urea being the corresponding enzymic substrate utilised to indicate the presence of antibodies or antigenic or haptenic substances in the sample. The presence of ammonia produced by the action of the enzyme urease on the urea substrate is then used to indicate the presence of antibodies or antigenic or haptenic substances in the sample. This improved ELISA technique has wide application, not only in connection with the use of the apparatus disclosed above and in the prior specification, but also as a general ELISA technique for use in association with known apparatus such as plates, wells and the like.

According to this aspect of the invention, there is provided a method of detecting or determining the presence of antibodies or an antigenic or haptenic substance in a sample by the enzyme-linked immunosorbent assay technique in which the binding of an antibody-enzyme or antigen-enzyme conjugate to a solid phase is used to indicate the presence or absence of antibodies or antigenic or haptenic substance in said sample, characterised in that the enzyme in said conjugate is urease, the solid phase is contacted with urea as the enzyme substrate, and the presence of ammonia is detected or determined using di-bromo-o-cresolsulfonphthalein to indicate the presence of antibodies or antigenic or haptenic substances in the sample. In general, in this aspect the present invention may be adapted to perform a wide variety of assay procedures. The following are illustrative, but by no means limiting, of the types of procedures which may be performed:

A: Antigen detection, e.g. hepatitis, digoxin.
  (a) Sandwich antigen assay:
    1. Solid phase: Tube - Anti-hepatitis Ab
    2. Sample: ±Hepatitis subunit or virus
    3. Conjugate: Anti-hepatitis Ab - enyzme
  (b) Double antibody sandwich antigen assay:
    1. Solid Phase: Tube - Anti-hepatitis Ab Type 1 (e.g. sheep antibody)
    2. Sample: ±Hepatitis subunit or virus
    3. Second Antibody: Anti-hepatitis Ab Type 2 (e.g. rabbit antibody)
    4. Conjugate: Anti-type 2 Ab - enzyme
  (c) Competitive antigen assay:
    1. Sample: ±Digoxin
    2. Conjugate: Anti-digoxon Ab - enzyme
    3. Solid phase: Tube - Digoxin
(Note: In this assay specimen and conjugate are mixed and incubated prior to addition to tube.)
B: Antibody detection, e.g. tetanus, rubella.
  (a) Sandwich antibody assay:
    1. Solid phase: Tube - Tetanus Ag
    2. Sample: ±Anti-tetanus Ab (Human)
    3. Conjugate: Anti-human Ab - enzyme.
  (b) Double antibody sandwich antibody assay:
    1. Solid phase: Tube - Tetanus Ag
    2. Sample: ±Tetanus Ab (Human)
    3. Second Antibody: Anti-human Ab Type 2 (e.g. sheep antibody against human antibody).
    4. Conjugate: Anti-type 2 Ab - enzyme.

In a first preferred embodiment of this aspect of the present invention, there is provided a method of detecting or determining the presence of an antigenic or haptenic substance in a sample which comprises, in sequence, the steps of:
1. contacting the sample with a solid phase having antibody corresponding to the said antigenic or haptenic substance attached thereto, and then contacting the solid phase with an antibody-enzyme conjugate;
2. contacting the sample with an antibody-enzyme conjugate, the antibody in the conjugate being antibody corresponding to the said antigenic or haptenic substance and enzyme in the conjugate being urease, and then contacting the resulting mixture with a solid phase having said antigenic or haptenic substance attached thereto;
3. contacting the solid phase with urea as the enzymic substrate; and
4. detecting or determining the presence of ammonia using di-bromo-o-cresolsulfonphthalein indicator to indicate the presence of said antigenic or haptenic substances in said sample.

In a second preferred embodiment, the present invention provides a method of detecting or determining the presence of antibodies in the sample which comprises, in sequence, the steps of:
1. contacting the sample with a solid phase having antigen corresponding to said antibodies attached thereto;
2. contacting the solid phase with an antibody-enzyme conjugate, the antibody in said conjugate being directed against the animal species of said antibodies under test and the enzyme in said conjugate being urease;
3. contacting the solid phase with urea as the enzymic substrate; and
4. detecting or determining the presence of ammonia using di-bromo-o-cresolsulfonphthalein indicator to indicate the presence of said antibodies in said sample.

In yet another aspect, this invention provides a test kit for the detection or determination of the presence of antibodies or an antigenic or haptenic substance in a sample by the enzyme-linked immunosorbent assay technique in which the binding of an antibody-enzyme or antigen-enzyme conjugate to a solid phase is used to indicate the presence or absence of antibodies or antigenic or haptenic substances in said sample, said kit comprising an antibody-enzyme or antigen-enzyme conjugate, the enzyme in said conjugate being urease, and a substrate/indicator system comprising urea as the enzyme substrate and di-bromo-o-cresolsulfonphthalein as indicator.

It will be appreciated that test kits as generally described above may be set up with appropriate components to enable the performance of the wide variety of assay procedures previously mentioned including the so-called "sandwich" and "competitive" assays, and the double-antibody type assays.

In a first preferred embodiment of this aspect, there is provided a test kit for the detection or determination of the presence of an antigenic or haptenic substance in a sample, said kit comprising, in combination:

1. a solid phase having antibody corresponding to the said antigenic or haptenic substance attached thereto;
2. an antibody-enzyme conjugate, the enzyme in said conjugate being urease; and
3. a substrate/indicator system comprising urea as the enzymic substrate and di-bromo-o-cresolsulfonphthalein as indicator.

Similarly, in a second preferred embodiment of this aspect, the invention also provides a test kit for the detection or determination of the presence of antibodies in a sample, said kit comprising, in combination:

1. a solid phase having antigen corresponding to said antibodies attached thereto;
2. an antibody-enzyme conjugate, the enzyme in said conjugate being urease; and
3. a substrate/indicator system comprising urea as the enzymic substrate and di-bromo-o-cresolsulfonphthalein as indicator.

The present invention further provides in combination and individually, antibody-enzyme conjugates and substrate-indicator systems, as described above.

The improvement now provided in these further aspects resides in the use of the particular indicator di-bromo-o-cresolsulfonphthalein, or Bromcresol Purple, as the indicator of the presence of ammonia. The production of ammonia may be readily detected by a pH shift which has been found to be best detected by the vivid colour change (yellow to purple) of Bromcresol Purple incorporated in an unbuffered substrate solution. The use of urease-urea as an enzyme-substrate system offers a number of important advantages: the substrate, being stable, may be stored ready to use; titration end points are sharp and readily visible; the enzyme is not poisoned by sodium azide and therefore test reagents may be prepared with this preservative and stored ready to use (this is not the case with Horse Radish Peroxidase (HRP), an enzyme which has been used in EIA tests previously). These factors therefore make the enzyme suitable for EIA kits intended for field use. The enzyme is commercially available at a higher specific activity than other commonly used enzyme labels and, because urease does not occur in mammalian tissues whereas other enzymes such as peroxidases, phosphatases and galactosidases may occur in such tissues, it is suitable for use in EIA tests to detect cell-associated antigens and their antibodies. Finally, the enzyme reaction may, if desired, be stopped instantly by the addition of the organo mercurial preservative Thiomersal, thus allowing storage of EIA results for later examination.

The fact that Bromcresol Purple is of particular benefit as an indicator in the methods described above is surprising, since the colour change provided by Bromcresol Purple takes place in the pH range of 5.2 to 6.8. Urease, on the other hand, has a maximum activity of pH's in the range of 7 to 8. It has, nevertheless, been found that the use of Bromcresol Purple to detect the presence of ammonia is effective in giving a complete and quite rapid colour change. In contrast, other pH indicators tested do not give a comparable colour change or exhibit a similar rapidity of reaction for a given concentration of antigenic substance, for example, snake venom. FIG. 1 of the accompanying drawings illustrates the sensitivity of Bromcresol Purple (BCP) as an indicator of the presence of ammonia produced by the action of urease on urea, when compared with the other pH indicators Cresol Red (CR), Bromthymol Blue (BTB), Chlorophenol Red (CPR) and Phenol Red (PR), all of which also provide a colour change in the pH range of 5 to 8, as set out in Table 1 below.

TABLE 1

| Indicator | Abbr. | λmax (nm) of anion | pH initial | pH range of colour change | Nature of colour change |
|---|---|---|---|---|---|
| Bromcresol Purple | BCP | 590 | 5.0 | 5.2–6.8 | yellow → violet |
| Cresol Red | CR | 572 | 6.5 | 7.2–8.8 | yellow → red |
| Bromothymol Blue | BTB | 648 | 6.0 | 6.0–7.6 | yellow → blue |
| Chlorophenol Red | CPR | 568 | 5.1 | 5.2–6.8 | yellow → red |
| Phenol Red | PR | 555 | 6.6 | 6.6–8.0 | yellow → red |

It will be apparent from FIG. 1, that in an unbuffered system, the pH indicators BCP, BTB and PR give linear absorbance-versus-time plots, whereas CR and CPR give curved responses. In addition BCP is much more sensitive than the other indicators and gives a marked yellow to purple colour shift which can be readily detected visually as these colours are spaced far apart in the visible light spectrum. BCP therefore provides a number of advantages as indicator for use in EIA tests involving urease when compared to the other pH indicators which would be expected to give higher reaction rates and thus be more sensitive at the pH optimum of urease in the EIA system. Bromcresol Purple is also particularly advantageous when compared with the use of the Nessler reaction to detect the formation of ammonia, as the use of a pH indicator provides a continuous measurement of urease activity and does not destroy the enzyme as in the use of the Nessler reaction. Accordingly, the use of Bromcresol Purple is of particular advantage in performing assays using urease/urea as the enzyme/substrate system in ELISA techniques.

In a further significant improvement of the test procedures of this aspect of the invention, it has been discovered that the occurrence of non-specific binding during the test procedure, particularly of the antibody-enzyme conjugate to the solid phase, can be dramatically reduced by the incorporation of ovalbumin in the antibody-enzyme conjugate reagent. In general, this reagent comprises the conjugate carried in a standard diluting buffer, for example, buffered saline (pH 7.2) containing 0.5% by weight, surfactant (Tween 20) 0.25% by weight, bovine serum albumin, and 0.1% by weight, preservative (sodium azide). In accordance with this further development, ovalbumin is added to this reagent in an amount of 0.1% by weight or greater, preferably from 0.25% to 1% by weight.

The devices and methods according to the present invention are illustrated, by way of example, in and by reference to the accompanying drawings, in which:

FIG. 2 is a part-sectional view through a first embodiment of a device in accordance with the invention; and FIG. 3 is a part-sectional view of a second embodiment of a device in accordance with the invention.

Figure 1:
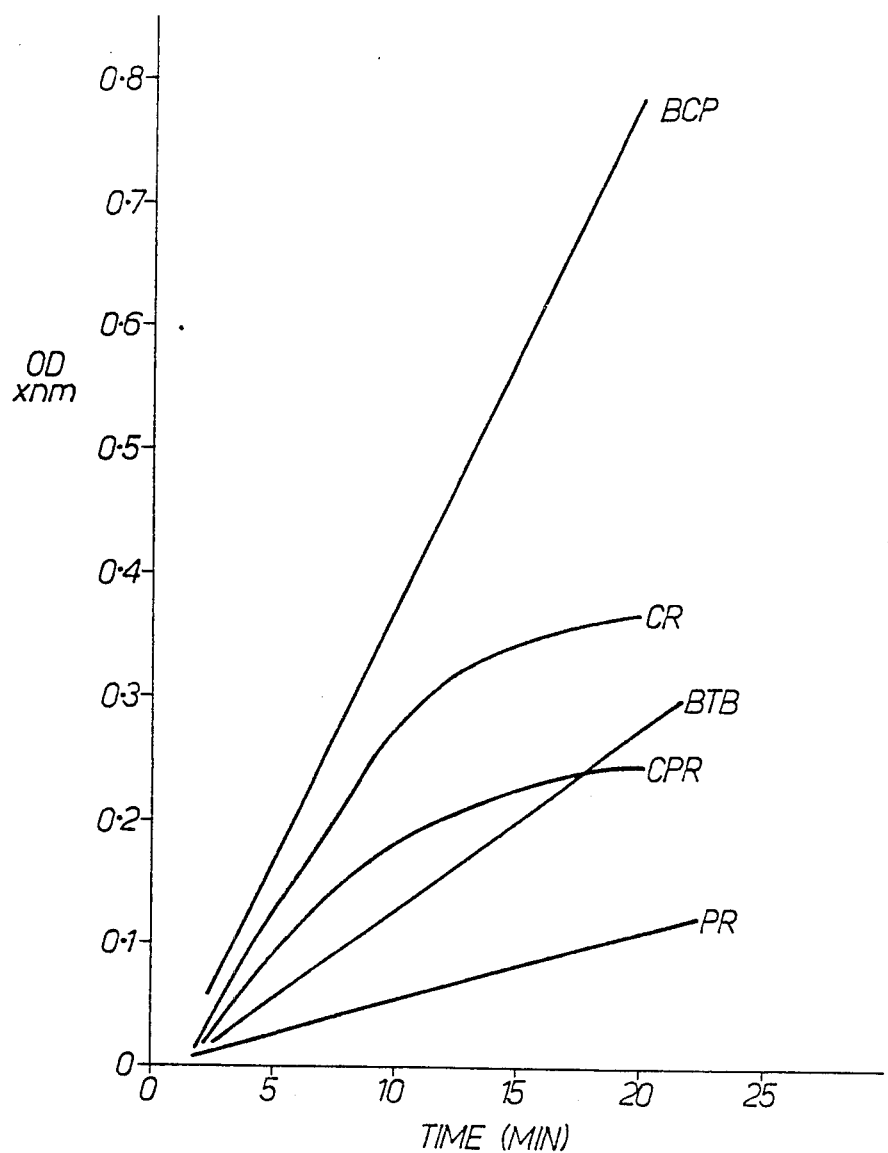
FIG. 1 is a plot of light absorbance versus time.

The device depicted in FIG. 2 is designed particularly for use as a snake venom detection apparatus, and will be described hereinafter with particular reference to its use in this manner. The device comprises a glass tube assembly 10, and a syringe 11 which is arranged to draw fluids into and expel fluids from the glass tube assembly 10. Assembly 10 comprises six tubular elements 1, 2, 3, 4, 5, 6, which are joined in series by pieces of silicone rubber tubing 8. Each of the tubes 1 to 5 has a different antivenom adhering to its internal surface as follows:

Tube 1: Tiger Snake
Tube 2: Brown Snake
Tube 3: King Brown Snake
Tube 4: Death Adder
Tube 5: Taipan In addition, tube 6 is provided as a control positive tube. The free end of tube 6 is sealed by means of a sealed plastic tube 7 which, in contrast to the transparent tubes 1 to 5, may be coloured, or opaque. The device illustrated in FIG. 2 of the drawings is used in the detection and identification of snake venoms in combination with a number of solution-containing bottles as follows:

Bottle 1: Contains washing buffer
Bottle 2: Contains antibody-enzyme conjugate, i.e. antivenom coupled to urease, in buffered saline
Bottle 3: Contains washing liquid (unbuffered)
Bottle 4: Contains enzyme substrate and indicator, i.e. urea solution, Bromcresol Purple and EDTA (to complex any metal ions which may poison the urease).

The following procedure is followed in performing the test:

(1) Check the joints between tubes of the device are secure. Immediately before use cut sealed tip from plastic tube and expel liquid from tubes.
(2) Draw clinical sample until tube assembly filled.
(3) Allow to rest at room temperature for approximately 10 minutes.
(4) Expel contents (waste). Draw in wash (Bottle 1) until syringe half full (approx.). Expel (waste). Repeat 3 times.
(5) Draw air, followed by conjugate (Bottle 2), until all tubes filled.
(6) Allow to rest at room temperature for approximately 10 minutes.
(7) Expel contents (waste). Draw in wash (Bottle 3) until syringe half full (approx.). Expel (waste). Repeat 3 times.
(8) Draw air, followed by substrate (Bottle 4), until all tubes filled.
(9) Observe carefully against a white background for 20 minutes from step 8. All snake venoms cross-react immunologically therefore note the first tube to follow the colour change sequence of yellow-green-grey-blue-purple shown by the positive control tube 6.

It will be noted that in the test described above, the indicator used to detect the production of ammonia in the urease/urea system is Bromcresol Purple. As previously described, this indicator has been found to be of particular benefit in this system and it is found that the detection limit of the test as performed above is approximately 10 to 20 nanograms/ml of sample used in step 2. Furthermore, greater sensitivity may be achieved by repeating the test using longer incubations for steps 3 and 6 (for example of the order of 20 to 30 minutes). As previously described, however, the use of this indicator in the urease/enzyme system is by no means restricted to use with the devices disclosed in the present specification or in the prior specifications referred to above, and those skilled in the art will appreciate that it has wide application as a general indicator for detecting urease activity in ELISA procedures using other apparatus. Similarly, the device described in detail above is not restricted to use in the detection of snake venoms, and it has application in the detection of tetanus antibodies as described in the prior specifications referred to above, as well as in other screening tests utilising the ELISA technique.

The device depicted in FIG. 3 illustrates an alternative embodiment of the device of the invention for use, for example, in a digoxin or tetanus screening test, and will be described hereinafter with particular reference to its use in this manner.

The device 20 comprises three glass tubular or capillary elements 21, 22 and 23 mounted in a common body or support 24. Each of these elements has a haptenic substance adhering to its internal surface as described below. Support 24 is also provided with three bores 25, 26 and 27 which communicate with elements 21, 22 and 23, respectively. Plungers 28, 29 and 30 are located within bores 25, 26 and 27, respectively, and are adapted to draw fluids through the respective capillary elements and into the bores, and to express these fluids out through the respective elements on movement of the plungers within the bores. Plungers 28, 29 and 30 are interconnected by a single handle piece 31 so that fluids are simultaneously drawn into and expressed from each of the capillary elements 21, 22 and 23. A white background area 32 is provided behind a portion of elements 21, 22 and 23 to assist in visual comparison of colour development in these elements.

The device 20 may be used in a digoxin screening test based on the inhibition of urease- anti-digoxin antibody conjugate binding to digoxin immobilised on the inner surface of the glass capillary elements caused by free digoxin present in the unknown serum. This test may be designed to detect digoxin in the serum of patients at levels below 1.0 nanograms/ml, between 1.0 and 3.0 nanograms/ml, and above 3.0 nanograms/ml. The accepted therapeutic range for digoxin is between 1.0 and 3.0 nanograms/ml, serum levels below this range may be ineffective, serum levels above this range may be toxic. This simple screening test enables the physician to estimate patient compliance with prescribed medication and, in cases of suspected toxicity, to rapidly confirm the diagnosis.

Due to the haptenic nature of digoxin, this test works on the inhibition of colour development which is in contrast to the snake venom detection test described above. The unknown sample of patient's serum and urease-anti-digoxin conjugate are preincubated together in a test tube or well of a reagent tray. Simultaneously known positive serum samples (1 nanogram/ml and 3 nanogram/ml free digoxin) are pre-incubated with conjugate in adjacent tubes or wells. After a predetermined incubation period at room temperature, the mixtures are simultaneously drawn into respective capillary elements 21, 22 and 23, each of which has digoxin conjugated to human serum albumin covalently attached to the inner surface thereof. After a further incubation period, the mixtures are expressed out of the elements 21, 22 and 23, the elements are washed and the urea indicator previously described simultaneously drawn into the elements. The amount of inhibition of colour development in the case of the unknown sample is then compared to that seen in the cases of the sera containing known amounts of free digoxin to provide a semi-quantitative assay of the unknown sample.

An alternative use of the device 20 is in a tetanus screening assay in which a sample of the blood or serum of a patient is screened against reference serums or blood to ascertain the level of tetanus antibodies in the sample. The assay is based on detection of tetanus antibodies binding to purified tetanus antigen immobilised on the inner surfaces of the glass capillary elements, the procedure comprising incubating the sample serum or blood and high (for example at least 1.28 International Units/ml) and low (for example no greater than 0.01 International Units/ml) reference sera or bloods within individual elements 21, 22 and 23 of the device 20 for a period of about 10 minutes, and after appropriate washing introducing anti-human Ab (IgG) - urease conjugate and incubating for a further period of about 10 minutes. After further washing the substrate/indicator system comprising urea and Bromcresol Purple as previously described is introduced and the colour development in the sample test compared with that in the high and low reference tests to indicate the tetanus antibody titre in the sample.

By using the assay outlined above, the sample can be classified into one of three categories:
(a) A titre equal to or greater than the high reference titre
   indicates patient highly immune and probably does not require booster vaccination (which would possibly involve risk of adverse reaction).
(b) A titre between the high and low reference titres
   indicates patient immune but a booster vaccination probably warranted.
(c) A titre equal to or less than the low reference titre
   indicates patient non-immune and in cases of injury administration of tetanus immune globulin and vaccine probably warranted.

In each of the examples set out above, the urease conjugate is prepared by standard procedures, either by the single step glutaraldehyde method Aurameas, S., Ternynck, T. and Guesdon, J. L., "Coupling of enzymes to antibodies and antigens", 1978 Scand. J. Immunol. 8 (Suppl.7), pp. 7–23) or by the M.B.S. method (Monji, N., Malkus, H. and Castro, A., "Maleimide derivative of hapten for coupling to enzyme: A new method in enzyme immunoassay" Biochem. Biophys. Res. Comm., 85, 671 (1978)). The conjugate reagent is made up in buffered saline (pH 7.2) as described in detail above, and includes ovalbumin in an amount of from 0.25% to 1% by weight to minimise non-specific binding of the conjugate.

The substrate solution comprises a dilute urea solution, for example containing 1 mg/ml of urea in glass distilled water, to which is added EDTA to complex heavy metal ions which may poison the urease.

Those skilled in the art will appreciate that the invention described herein is susceptible to variations and modifications other than those specifically described without departing from the broad teaching herein. It is to be understood that the invention includes all such modifications and variations which fall within its spirit and scope.

We claim:
1. A test kit for use in detecting or determining the presence of any member selected from the group consisting of antigenic substances, haptenic substances, and antibodies in a sample by an enzyme-linked immunosorbent assay technique, which comprises:
   (i) a plurality of capillary elements, each of said capillary elements having any member selected from the group consisting of antigenic substances, haptenic substances, and antibodies attached to an internal surface thereof, and means for causing fluids to pass simultaneously through said plurality of capillary elements;
   (ii) an antibody-enzyme or antigen-enzyme conjugate wherein when antigenic or haptenic substances are attached to the plurality of capillary elements, the conjugate is an antigen-enzyme conjugate and when antibodies are attached to the plurality of capillary elements, the conjugate is an antibody-enzyme conjugate; and
   (iii) an enzyme substrate/indicator system, wherein said capillary elements are connected in series by tubular connecting elements, and said series of elements is connected to a single means for causing fluids to pass therethrough.

2. A test kit for use in detecting or determining the presence of any member selected from the group consisting of antigenic substances, haptenic substances and antibodies in a sample by an enzyme-linked immunosorbent assay technique, which comprises:
   (i) a plurality of capillary elements, each of said capillary elements having any member selected from the group consisting of antignic substances, haptenic substances, and antibodies attached to an internal surface thereof, and means for causing fluids to pass simultaneously or sequentially through said plurality of capillary elements;
   (ii) an antibody-enzyme or antigen-enzyme conjugate wherein when antigenic or haptenic substances are attached to the plurality of capillary elements, the conjugate is an antigen-enzyme conjugate and when antibodies are attached to the plurality of capillary elements, the conjugate is an antibody-enzyme conjugate, the enzyme in said conjugate being urease; and
   (iii) an enzyme substrate/indicator system comprising urea as the enzyme substrate and di-bromo-O-cresol sulfonphthalein as said indicator.

3. A test kit according to any one of claim 2 wherein said capillary elements are constructed of glass or plastics materials, and said member selected from the group consisting of antigenic substances, haptenic substances and antibodies are attached to the internal surfaces thereof by adsorption or covalent bonding.

4. A test kit as claimed in claim 2, wherein said capillary elements have a capacity of about 5–20 microliters.

5. A test kit according to claim 2, wherein said capillary elements are connected in series by tubular connecting elements, and said series of elements is connected to a single means for causing fluids to pass therethrough.

6. A test kit according to claim 1, wherein said single means for causing fluids to pass through said series of capillary elements comprises a syringe device having means defining a bore in fluid communication with an end of one of said series of capillary elements, and a plunger movable within said bore.

7. A test kit according to claim 2, wherein said capillary elements are mounted side-by-side in a support and in fluid communication with means defining bores within said support, and said means for causing fluids to pass through said capillary elements comprises means for simultaneously drawing fluids into and expressing said fluids out of the bores through the respective capillary elements.

8. A test kit according to claim 7, wherein individual plungers are mounted within said bores for movement relative thereto to draw fluids into and express fluids out of said bores, and said individual plungers are interconnected for simultaneous movement relative to the respective bores.

* * * * *